United States Patent
Sato et al.

(10) Patent No.: US 7,217,560 B2
(45) Date of Patent: May 15, 2007

(54) PROCESS FOR PREPARATION OF OPTICALLY ACTIVE PROPOXYANILINE DERIVATIVES

(75) Inventors: Kouji Sato, Tokyo (JP); Tsutomu Yagi, Tokyo (JP); Kazuo Kubota, Tokyo (JP); Akihiro Imura, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 424 days.

(21) Appl. No.: 10/469,827

(22) PCT Filed: Mar. 6, 2002

(86) PCT No.: PCT/JP02/02054

§ 371 (c)(1),
(2), (4) Date: Sep. 5, 2003

(87) PCT Pub. No.: WO02/070726

PCT Pub. Date: Sep. 12, 2002

(65) Prior Publication Data

US 2004/0077060 A1 Apr. 22, 2004

(30) Foreign Application Priority Data

Mar. 7, 2001 (JP) .............................. 2001-63945

(51) Int. Cl.
*C12P 41/00* (2006.01)
(52) U.S. Cl. .................................................. 435/280
(58) Field of Classification Search ..................... None
See application file for complete search history.

(56) References Cited

U.S. PATENT DOCUMENTS

| 4,985,365 | A | * | 1/1991 | Mitsuda et al. | ............. | 435/280 |
| 5,108,916 | A | * | 4/1992 | Cobbs et al. | ............. | 435/135 |
| 5,302,528 | A | * | 4/1994 | Battistel et al. | ............. | 435/280 |

FOREIGN PATENT DOCUMENTS

| EP | 0 206 283 A2 | 12/1986 |
| EP | 322815 | 7/1989 |
| JP | 61-135600 | 6/1986 |
| JP | 63-63397 | 3/1988 |
| JP | 2-156892 | 6/1990 |
| JP | 5-68577 | 3/1993 |

OTHER PUBLICATIONS

ATCC Bacteria and Bacteriophages, 19th Edition, p. 215 (1996).*
S. E. Maloney, et al., "Purification and Preliminary Characterization of Permethrinase from a Pyrethroid-Transforming Strain of *Bacillus cereus*", Applied and Environmental Microbiology, vol. 59, No. 7, XP-002373808, Jul. 1993, pp. 2007-2013.

Hiroh Ikezawa, et al., "Studies on Phosphatidylinositol Phosphodiesterase (Phospholipase C Type) of *Bacillus cereus*", Biochimica et Biophysica Acta, vol. 450, No. 2, XP-002373809, Nov. 19, 1976, pp. 154-164.
Lester A. Mitscher, et al., "Chiral DNA Gyrase Inhibitors. 2. Asymmetric Synthesis and Biological Activity of the Enantiomers of 9-Fluoro-3-methyl-10-(4-methyl-1-piperazinyl)-7-oxo-2,3-dihydro-7H-pyrido[1,2,3-de]-1,4-benzoxazine-6-carboxylic Acid (Ofloxacin)", J. Med. Chem., vol. 30, No. 12, XP-002358017, 1987, pp. 2283-2286.
Shohgo Atarashi, et al., "Synthesis and Antibacterial Activities of Optically Active Ofloxacin and Its Fluoromethyl Derivative", Chem. Pharm. Bull., vol. 35, No. 5, XP-002991710, 1987, pp. 1896-1902.

* cited by examiner

*Primary Examiner*—Sandra E. Saucier
(74) *Attorney, Agent, or Firm*—Oblon, Spivak, McClelland, Maier & Neustadt, P.C.

(57) ABSTRACT

Treatment of a lactic acid ester derivative with an enzyme or the like, which has asymmetric ester-hydrolyzing ability, can specifically hydrolyze the ester moiety of an isomer existing as the pair to the racemic derivative. Use of the compound obtained by this hydrolysis makes it possible to produce an optically active propoxyaniline derivative by a shorter process than the conventional art

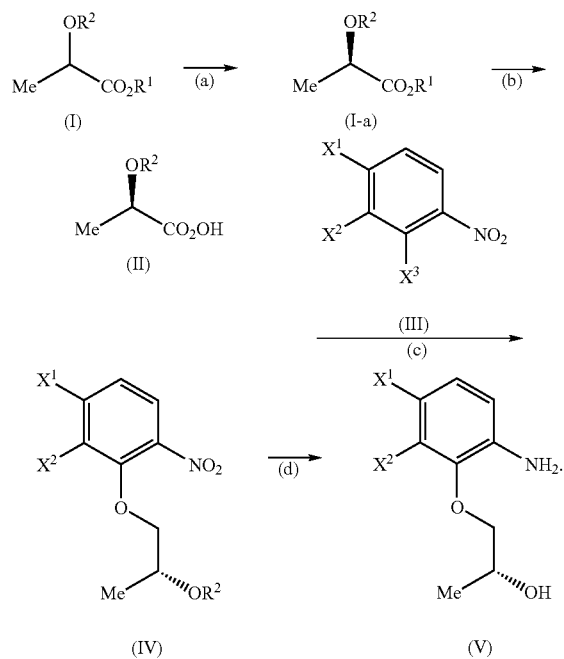

12 Claims, No Drawings

PROCESS FOR PREPARATION OF OPTICALLY ACTIVE PROPOXYANILINE DERIVATIVES

The present application is a national stage application of PCT/JP02/02054, filed Mar. 6, 2002.

TECHNICAL FIELD

This invention relates to a process for producing optically active propoxyaniline derivatives useful in the production of antimicrobial compounds and also to a process for producing intermediates therefor.

BACKGROUND ART

S-(−)-9-Fluoro-3-methyl-10-(4-methyl-1-piperazinyl)-7-oxo-2,3-dihydro-7H-pyrido[1,2,3-de] [1,4]benzoxazine-6-carboxylic acid (levofloxacin, LVFX; JP 62-252790 A) is known as an excellent synthetic antibacterial agent.

There has been a compound known to be useful as an intermediate for producing this synthetic antibacterial agent, which is represented by the following formula (V):

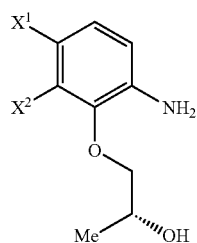

(V)

wherein $X^1$ and $X^2$ each independently represents a halogen atom (hereinafter referred to as "Compound (V)"; similar symbolic marks will be applied to other formulae). This compound is known to be producible through the following process (JP 1-250369 A and JP 2-723 A).

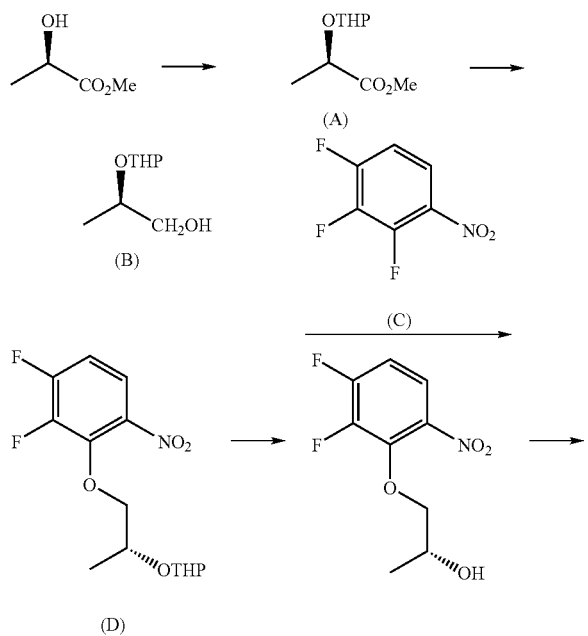

-continued

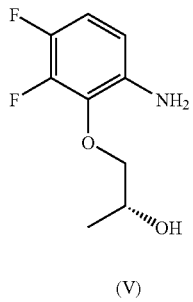

(V)

That is to say, compound (V) can be synthesized by reducing compound (A), prepared beforehand by protecting the hydroxyl group of a commercially available lactic acid ester with a tetrahydropyranyl group, with lithium aluminum hydride to obtain compound (B), treating compound (B) and compound (C) in the presence of sodium hydride to obtain compound (D), and then removing the tetrahydropyranyl group, followed by reducing the nitro group.

The lactic acid esters serving as a raw material of compound (A) are commercially available at low cost, but the optical purity of such esters is limited to 97% ee at most, so they are not adequate as a raw material of the levofloxacin compound required to satisfy a high purity of at least 99% ee.

For the production of the compound (B), another process has also been developed without using any lactic acid ester (JP 2-265701 A). On the other hand, a large amount of lithium aluminum hydride is too difficult to handle for reduction, because of its safety problem. The aforementioned production process also demands relatively many steps. Furthermore, it has been reported that unnecessary recemization could be caused by the removal of tetrahydropyranyl group from compound (D) (S. Chladek, Chem. Ind. (London), 1719 (1964)).

Owing to the forgoing problems, several researches have so far been carried out using a compound ((R)-2-benzyloxypropionic acid ester) whose structure is close to compound (A) except that the tetrahydropyranyl group is replaced with a benzyl group. However, it has been impossible to obtain any compound other than those having a poor optical purity limited to 97% ee at most. Levofloxacin as a drug is required to have much higher optical purity of at lease 99% ee, but it is extremely difficult to improve the optical purity in intermediate steps. (R)-2-Benzyloxypropionic acid esters of 97% ee or less are not usable as raw materials for levofloxacin.

Hence, there has been a long standing demand for the development of a process not affected by these problems.

An object of the present invention is to provide an economical and efficient process for the production of an optically active propoxyaniline derivative and levofloxacin useful as an antimicrobial agent and also to provide processes for the production of intermediates for the foregoing process.

Another object of the present invention is to provide an enzyme having asymmetric ester-hydrolyzing ability and obtained by disrupting cells of a microorganism, which has asymmetric ester-hydrolyzing ability, under high pressure and then purifying the thus-disrupted cells successively by strong anion chromatography, hydrophobic chromatography and strong anion chromatography.

DISCLOSURE OF THE INVENTION

As a result of their extensive study, the present inventors have found a method characterized by treating a racemic lactic acid derivative with an enzyme having asymmetric ester-hydrolyzing ability, and then specifically hydrolyzing the ester moiety of an isomer existing as the pair to this racemic derivative, and have also found that when the compound obtained by this hydrolysis is used as an intermediate, it is possible to produce an optically active propoxyaniline derivative at lower cost, as well as through fewer steps, than any other methods. Besides, the present inventors have found a method for recycling an optical isomer, which emerges as an unwanted by product in the course of an asymmetric ester-hydrolyzing reaction, into a substrate by racemizing said optical isomer. Based on these findings, the present inventors have discovered that a levofloxacin compound having a high optical purity can be produced efficiently. Thus, this invention was accomplished.

Specifically, the present invention provides a process for producing an optically active compound represented by the following formula (I-a):

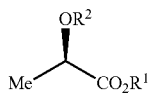

(I-a)

wherein $R^1$ represents an alkyl group having 1 to 6 carbon atoms and $R^2$ represents a hydroxyl-protecting group, which comprises:

treating a compound, which is represented by the following formula (I):

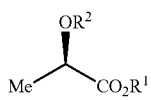

(I)

wherein $R^1$ and $R^2$ have the same meanings as defined above, with an enzyme having asymmetric ester-hydrolyzing ability, a cultured medium of a microorganism having asymmetric ester-hydrolyzing ability, cells of the microorganism or a processed product of cells of the microorganism to obtain a mixture; and isolating and collecting the optically active compound (I-a) from the mixture.

The present invention also provides a process for producing a compound represented by the following formula (V):

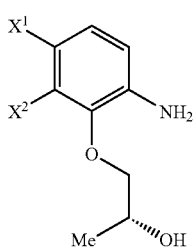

(V)

wherein $X^1$ and $X^2$ each independently represents a halogen atom, which comprises:

treating a compound, which is represented by the following formula (I):

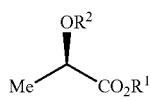

(I)

wherein $R^1$ and $R^2$ have the same meanings as defined above, with an enzyme having asymmetric ester-hydrolyzing ability, a cultured medium of a microorganism having asymmetric ester-hydrolyzing ability, cells of the microorganism or a processed product of cells of the microorganism to obtain a mixture, and isolating, collecting and obtaining from the mixture an optically active compound represented by the following formula (I-a):

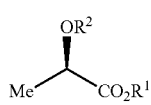

(I-a)

wherein $R^1$ and $R^2$ have the same meanings as defined above;

treating the compound (I-a) with a metal borohydride compound in the presence of a primary alcohol in a non-alcoholic solvent to obtain a compound represented by the following formula (II):

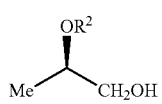

(II)

wherein $R^2$ has the same meaning as defined above;

treating the compound (II) and a compound, which is represented by the following formula (III):

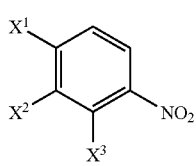

(III)

wherein $X^1$ and $X^2$ have the same meanings as defined above, and $X^3$ independently represents a halogen atom, in the presence of a base to obtain an optically active compound represented by the following formula (IV):

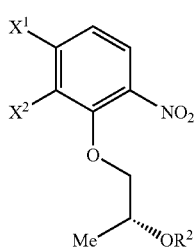

(IV)

wherein $R^2$, $X^1$ and $X^2$ have the same meanings as defined above; and conducting conversion of a nitro group into an amino group and removal of $R^2$ at the same time in the compound (IV).

The present invention also provides a process for producing a compound represented by the following formula (XII):

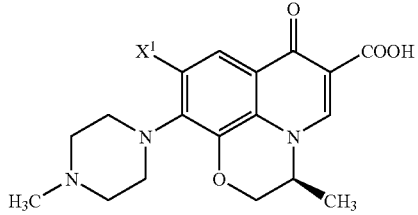
(XII)

wherein $X^1$ has the same meaning as defined above, which comprises:

treating a compound, which is represented by the following formula (I):

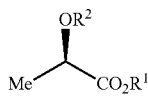
(I)

wherein $R^1$ and $R^2$ have the same meanings as defined above, with an enzyme having asymmetric ester-hydrolyzing ability, a cultured medium of a microorganism having asymmetric ester-hydrolyzing ability, cells of the microorganism or a processed product of cells of the microorganism to obtain a mixture, and isolating, collecting and obtaining from the mixture an optically active compound represented by the following formula (I-a):

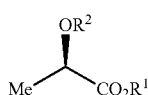
(I-a)

wherein $R^1$ and $R^2$ have the same meanings as defined above;

treating the compound (I-a) with a metal borohydride compound in the presence of a primary alcohol in a non-alcoholic solvent to obtain an optically active compound represented by the following formula (II):

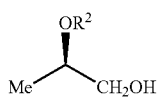
(II)

wherein $R^2$ has the same meaning as defined above;

treating the compound (II) and a compound, which is represented by the following formula (III):

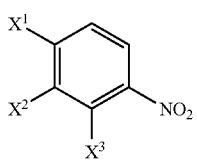
(III)

wherein $X^1$ and $X^2$ and $X^3$ have the same meanings as defined above, with a base to obtain an optically active compound represented by the following formula (IV):

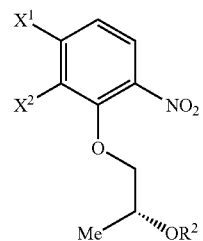
(IV)

wherein $R^2$, $X^1$ and $X^2$ have the same meanings as defined above;

conducting conversion of a nitro group into an amino group and removal of R at the same time in the compound (IV) to obtain a compound represented by the following formula (V):

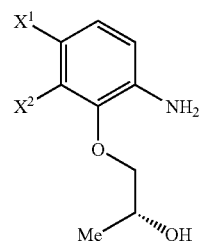
(V)

wherein $X^1$ and $X^2$ have the same meanings as defined above;

reacting the compound (V) with a compound, which is represented by the following formula (VI):

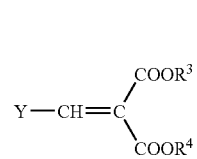
(VI)

wherein Y represents an alkoxy group having 1 to 6 carbon atoms, a halogen atom or a di($C_1$–$C_6$ alkyl)amino group and $R^3$ and $R^4$ each independently represents an alkyl group having 1 to 6 carbon atoms, to obtain a compound represented by the following formula (VII):

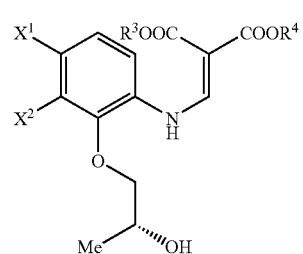
(VII)

wherein $X^1$, $X^2$, $R^3$ and $R^4$ have the same meanings as defined above;

reacting the compound (VII) with a sulfonyl compound to obtain a compound represented by the following formula (VIII):

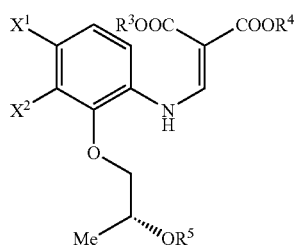

(VIII)

wherein $R^5$ represents a substituted or unsubstituted alkylsulfonyl group or a substituted or unsubstituted arylsulfonyl group, and $X^1$, $X^2$, $R^3$ and $R^4$ have the same meanings as defined above;

subjecting the compound (VIII) to a ring-closing reaction under basic conditions to obtain a compound represented by the following formula (IX):

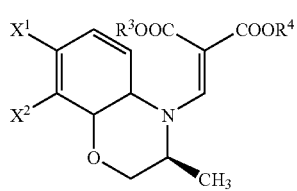

(IX)

wherein $X^1$, $X^2$, $R^3$ and $R^4$ have the same meanings as defined above;

heating the compound (IX) in the presence or absence of a boron compound to obtain a compound represented by the following formula (X):

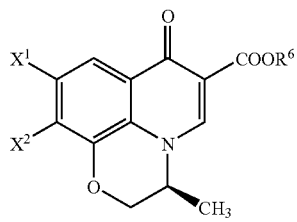

(X)

wherein $R^6$ represents an alkyl group having 1 to 6 carbon atoms or $BZ_2$ in which Z represents a halogen atom, a $C_1$–$C_6$ alkoxy group or a $C_2$–$C_7$ alkylcarbonyloxy group, and $X^1$ and $X^2$ have the same meanings as defined above;

reacting the compound (X) with 4-methylperazine to obtain a compound represented by the following formula (XI):

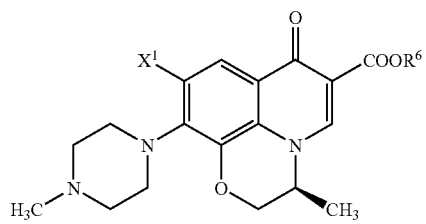

(XI)

wherein $X^1$ and $R^6$ have the same meanings as defined above; and hydrolyzing the compound (XI).

The present invention also provides an enzyme having asymmetric ester-hydrolyzing ability and obtained by disrupting cells of a microorganism, which has asymmetric ester-hydrolyzing ability, under high pressure and then purifying the thus-disrupted cells successively by strong anion chromatography, hydrophobic chromatography and strong anion chromatography.

BEST MODES FOR CARRYING OUT THE INVENTION

According to the present invention, the compound (I) is treated with an enzyme having asymmetric ester-hydrolyzing ability, a cultured medium of a microorganism having asymmetric ester-hydrolyzing ability, cells of the microorganism or a processed product of cells of the microorganism to obtain a mixture. From the mixture, the compound (I-a) is isolated and collected. This compound (I-a) is then treated with a metal borohydride compound to obtain the compound (II). The compound (II) and the compound (III) are treated in the presence of a base to obtain a compound (IV). By a reducing reaction, this compound (IV) is converted into the optically active propoxyaniline derivative through a single step. From the compound (IV), the compound (XII) useful as an antibacterial agent is then produced.

A reaction process diagram from the compound (I) to the compound (XII) by the present invention will be shown below.

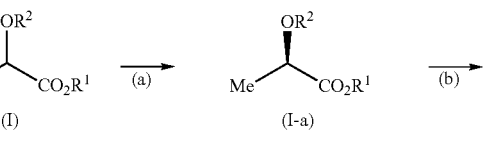

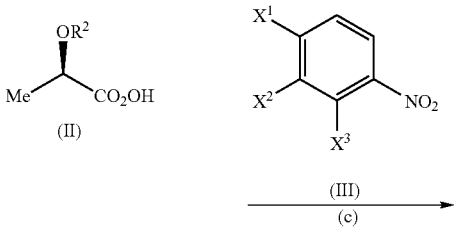

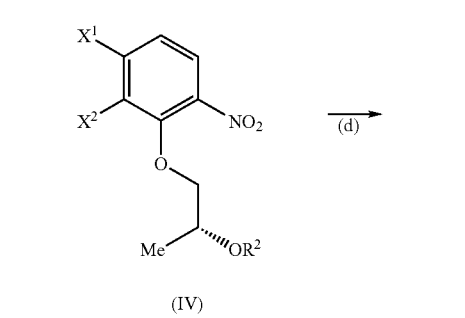

-continued

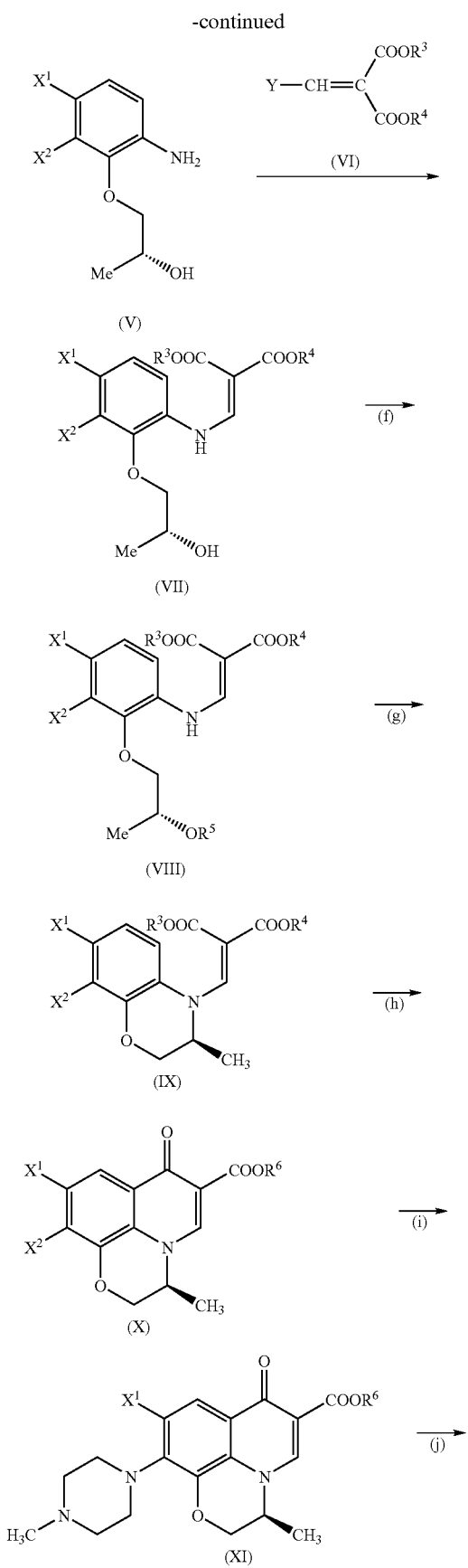

(V), (VI), (VII), (VIII), (IX), (X), (XI), (XII)

A description will be made about the substituents in the reaction scheme.

$X^1$, $X^2$ and $X^3$ each independently represents a halogen atom. As the halogen atom, a fluorine atom is preferred.

$R^1$, $R^3$ and $R^4$ each independently represents an alkyl group, which can be linear, branched or cyclic. Its carbon number may preferably be from 1 to 6. Particularly preferred are methyl, ethyl and isobutyl.

$R^2$ represents a hydroxyl-protecting group. No particular limitation is imposed on this protecting group insofar as it is one commonly employed. Illustrative are (substituted) alkoxycarbonyl groups, (substituted) aralkyloxycarbonyl groups, (substituted) acyl groups, (substituted) alkyl groups, (substituted) alkenyl groups, (substituted) aralkyl groups, and silyl groups substituted by one or more alkyl and/or aralkyl groups (which can be either the same or different) [It is to be noted that the term "(substituted)" as used herein means that a compound may contain one or more substituents.] Specific examples can include (substituted) alkoxycarbonyl groups such as tert-butoxy-carbonyl and 2,2,2-trichloroethoxycarbonyl; (substituted) aralkyloxycarbonyl groups such as benzyloxycarbonyl, paramethoxybenzyloxycarbonyl and paranitrobenzyloxy-carbonyl; (substituted) acyl groups such as acetyl, methoxyacetyl, trifluoroacetyl, chloroacetyl, pivaloyl, formyl and benzoyl; (substituted) aralkyl groups such as tert-butyl, allyl (propenyl), benzyl, paranitrobenzyl, paramethoxybenzyl, triphenylmethyl and phenethyl; (substituted) alkenyl groups and (substituted) aralkyl groups; ether groups such as methoxymethyl, tert-butoxymethyl, tetrahydropyranyl and 2,2,2-trichloroethoxymethyl; and substituted silyl groups such as trimethylsilyl, isopropyldimethylsilyl, tert-butyldimethylsilyl, tribenzylsilyl and tert-butyldiphenylsilyl. Among the above-exemplified protecting groups, preferred as $R^2$ is a (substituted) aralkyl group, with a (substituted) aralkyl group having the benzyl structure being more preferred. Particularly preferred is a benzyl group.

$R^5$ represents a (substituted) alkylsulfonyl group or a (substituted) arylsulfonyl group, with an alkylsulfonyl having 1 to 6 carbon atoms or a (substituted) benzenesulfonyl group being preferred. Among these, methanesulfonyl and p-toluenesulfonyl are particularly preferred.

$R^6$ represents a $C_1$–$C_6$ alkyl group or a $BZ_2$ in which Z represents a halogen atom, a $C_1$–$C_6$ alkoxy group or a $C_2$–$C_7$ alkylcarbonyloxy group. Examples of the alkoxy group having 1 to 6 carbon atoms can include methoxy, ethoxy, isopropoxy and tert-butoxy. Examples of the halogen atom can include those exemplified above in connection with $X^1$, $X^2$ and $X^3$. Examples of the $C_2$–$C_7$ alkylcarbonyloxy group can include acetyloxy, propionyloxy and butylyloxy. Of these, $BF_2$ is particularly preferred as $R^6$.

Y represents an alkoxy group having 1 to 6 carbon atoms, a halogen atom or a di ($C_1$–$C_6$ alkyl) amino group. Alkoxy groups having 1 to 6 carbon atoms are preferred, with methoxy and ethoxy being particularly preferred.

In the above-described reaction process diagram, the production process of only one of the isomers is shown. The other isomer can also be synthesized likewise provided that a compound similar to the compound (I-a) except that its configuration is reversed is used. Further, use of the compound (I) makes it possible to obtain the compound (V) in its racemic form.

The present invention will hereinafter be described step by step in detail.

Step (a)

The step (a) is a step in which the compound (I) is treated with an enzyme having asymmetric ester-hydrolyzing ability, a cultured medium of a microorganism having asymmetric ester-hydrolyzing ability, cells of the microorganism or a processed product of cells of the microorganism to obtain the compound (I-a).

Firstly, the compound (I) is suspended in an appropriate buffer, followed by the addition of the enzyme, the cultured medium of the microorganism, the cells of the microorganism or the processed product of cells of the microorganism. The resulting mixture is stirred to perform the treatment. No particular limitation is imposed on the enzyme employed in the reaction, insofar as it has asymmetric ester-hydrolyzing ability. Illustrative of the enzyme are commercial enzyme preparations derived from microorganisms, animals or plants.

As the enzyme for use in the present invention, lipase is preferred. Lipase may be in an immobilized form.

Illustrative of the microorganism are molds such as *Cladosporium* fungi, *Absidia* fungi, *Nannizzia* fungi, *Aspergillus* fungi, *Rhizopus* fungi and *Mucor* fungi; yeasts such as *Zygoacus* yeasts, *Candida* yeasts and *Saccharomyces* yeasts; and bacteria such as *Bacillus* bacteria, *Microbacterium* bacteria, *Micrococcus* bacteria, *Pseudomonas* bacteria, *Corynebacterium* bacteria and *Streptomyces* bacteria. Among these microorganisms, preferred are bacteria, more preferred are *Bacillus* bacteria and *Microbacterium* bacteria, still more preferred are *Bacillus cereus* and *Microbacterium laevaniformas*, and particularly preferred are *Bacillus cereus* (DSC 0007), *Bacillus cereus* (ATCC 14579) and *Microbacterium laevaniformas* (IFO 14471).

Illustrative of the processed product of cells of the microorganism, on the other hand, are a disrupted microbial cell mixture and purified products thereof.

In the present invention, use of these microorganisms, especially enzymes purified from cells of bacteria is preferred from the standpoint of reaction efficiency. Particularly preferred as such purified enzymes are those obtained by disrupting cells under high pressure and conducting purification successively by strong anion chromatography, hydrophobic chromatography and strong anion chromatography.

These purified enzymes can also be those obtained by treating ells as described above, and they can also be those produced in other hosts such as *Escherichia coli* by recombinant DNA technology. To obtain an enzyme by recombinant DNA technology, the following procedure can be mentioned by way of example. Firstly, the above-described purified enzyme is purified further by reverse phase chromatography, and the amino acid sequence of its protein is determined. Based on the amino acid sequence, a probe is prepared, and from DNA fragments of cells, a DNA encoding the active center of an asymmetric hydrolase is cloned. The DNA is then amplified by PCR to prepare a recombinant plasmid. This recombinant plasmid is introduced into *Escherichia coli* or the like. The *Escherichia coli* or the like is cultured to obtain the target enzyme.

By the above-described treatment, one of the optical isomers of the following compound (I):

wherein $R^1$ and $R^2$ have the same meanings as defined above is selectively hydrolyzed to form the following compound (I-b):

wherein $R^2$ has the same meaning as defined above, and the following unreacted compound (I-a):

wherein $R^1$ and $R^2$ have the same meanings as defined above can be isolated from the mixture. Described specifically, the compound (I-a) can be isolated and collected by adding an organic solvent such as ethyl acetate or chloroform to the mixture and then conducting treatment such as stirring and separation. Incidentally, the enzyme, cells or the like employed in the treatment may preferably be removed by filtration or the like before extraction of the compound (I-a).

The treatment temperature of each of these hydrolysis and isolation may generally be in a range of from 5° C. to 60° C., with a range of from 20° C. to 40° C. being preferred. The pH of each treatment solution may be in a range of from 4 to 9, with a range of from 6 to 8 being preferred. Each treatment time may be in a range of from 1 hour to 7 days, with a range of from 1 hour to 30 hours being preferred. Each treatment is generally conducted while controlling the concentration of the compound (I) in the treatment solution generally within a range of from 0.1% to 10%, preferably within a range of from 0.5% to 5% by weight. No particular limitation is imposed on the amount of the enzyme, the cultured medium of the microorganism, the cells of the microorganism or the processed product of cells of the microorganism to be used, but it is suited to use the enzyme, the cultured medium of the microorganism, the cells of the microorganism or the processed product of cells of the microorganism at a weight ratio of from 0.05 times to 0.5 times in terms of dry weight relative to the compound (I).

On the other hand, the compound (I-b) separated from the reaction mixture can recycled by subjecting it to an asymmetric ester-hydrolyzing reaction subsequent to its racemization after its esterification.

Step (b)

The step (b) is a step in which the compound (I-a) is treated with a metal borohydride compound in the presence of a primary alcohol in a non-alcoholic solvent to obtain the compound (II).

Illustrative of the metal borohydride compound are sodium borohydride, lithium borohydride, calcium borohydride, potassium borohydride, zinc borohydride, magnesium borohydride, and sodium cyanoborohydride. Of these, sodium borohydride is preferred. The amount of the metal borohydride compound to be used may be in a range of from 1 to 5 molar times, preferably from 1.1 to 2 molar times as much as the compound (I-a).

Illustrative of the solvent are hydrocarbon solvents such as n-hexane, n-pentane, cyclohexane and cyclopentane; aromatic hydrocarbon solvents such as benzene, toluene and xylene; ether solvents such as diethyl ether, diisopropyl ether (IPE), methyl tert-butyl ether (MTBE), tetrahydrofuran (THF), dimethoxyethane and 1,4-dioxane; and halogenated hydrocarbon solvents such as chloroform, methylene chloride and 1,2-dichloroethane (EDC). In addition, water, acetic acid esters and the like can also be mentioned. These solvents may be used either singly or in combination. Among these solvents, preferred are aromatic hydrocarbon solvents such as toluene and xylene.

No particular limitation is imposed on the primary alcohol, but methanol is preferred. The amount of the primary alcohol to be used may be in a range of from 3 to 15 molar times, preferably from 4 to 8 molar times or so relative to the compound (I-a).

The reaction temperature may differ depending upon the solvent to be used, but may range from −78° C. to the boiling temperature of the solvent, preferably from 10° C. to the boiling temperature of the solvent. The reaction time may be in a range of from 1 to 24 hours, preferably from 2 to 16 hours.

Step (c)

The step (c) is a step in which the compound (III) is obtained by treating the compound (II) in the presence of a base in a solvent.

A variety of solvents are usable as the solvent. Illustrative of the solvent are hydrocarbon solvents such as n-hexane and n-pentane; aromatic hydrocarbon solvents such as benzene, toluene and xylene; alcoholic solvents such as methanol, ethanol, propanol, isopropanol (IPA), n-butanol and tert-butanol; ether solvents such as diethyl ether, diisopropyl ether (IPE), methyl tert-butyl ether (MTBE), tetrahydrofuran (THF), dimethoxyethane and 1,4-dioxane; amide solvents such as N,N-dimethylformamide (DMF) and N,N-dimethylacetamide (DMAc); and halogenated hydrocarbon solvents such as chloroform, methylene chloride and 1,2-dichloroethane (EDC). In addition, water, acetonitrile, acetic acid esters, acetone and the like can also be mentioned. These solvents may be used either singly or in combination. Among these solvents, preferred are aromatic hydrocarbon solvents such as toluene and xylene.

The reaction temperature may differ depending upon the base and solvent to be used, but may range from −78° C. to the boiling temperature of the solvent, preferably from −10° C. to the boiling temperature of the solvent.

The base may be either organic or inorganic. Usable examples of the base can include the hydroxides, carbonates, hydrogencarbonates, alkoxides and the like of alkali metals or alkaline earth metals, for example, sodium, potassium, lithium, magnesium and calcium; metal hydrides such as sodium hydride, potassium hydride and lithium hydride; alkyllithium reagents such as n-butyllithium, methyllithium and lithium diisopropylamide; tertiary amines such as triethylamine and N,N-diisopropylethylamine; and further, heterocyclic compounds such as 1,8-diazobicyclo[5,4,0]undec-7-ene (DBU), 1,8-diazobicyclo[4,3,0]non-5-ene (DBN), dimethylaniline and N-methylmorpholine. To accelerate the reaction, the reaction, in some instances, may be conducted in the presence of a quaternary ammonium salt such as tetrabutylammonium bromide or benzyltriethylammonium chloride; an alkali metal or alkaline earth metal iodide, such as potassium iodide or sodium iodide; or a crown ether. Of these bases, preferred are alkali metal or alkaline earth metal carbonates such as potassium carbonate; alkali metal or alkaline earth metal hydroxides, such as potassium hydroxide; and alkali metal alkoxides such as tert-butoxy sodium and tert-butoxy potassium. Further, an alkali metal or alkaline earth metal carbonate, such as potassium carbonate, and an alkali metal or alkaline earth metal hydroxide, such as potassium hydroxide, may also be used in combination. The amount of the base to be used may be in a range of from 0.1 to 15 molar times, preferably from 1 to 5 molar times or so relative to the molar number of the compound (III).

Step (d)

The step (d) is a step in which the compound (V) is obtained by conducting the conversion of a nitro group into an amino group and the removal of $R^2$ at the same time in the compound (IV) through a reducing reaction.

The reducing reaction can be effected by conventional hydrogenation. For example, catalytic hydrogenation in the presence of a catalyst can be mentioned. Illustrative of a catalyst usable in this process are metal catalysts which are commonly employed. Among such metal catalysts, preferred are palladium-charcoal, Raney nickel, and Raney cobalt.

No particular limitation is imposed on the solvent insofar as it does not inhibit the reaction. Examples of the solvent can include hydrocarbon solvents such as n-hexane, n-pentane, benzene, toluene and xylene; and alcoholic solvents such as methanol, ethanol, propanol, isopropanol (IPA), n-butanol and tert-butanol. Illustrative ether solvents are diethyl ether, diisopropyl ether (IPE), methyl tert-butyl ether (MTBE), tetrahydrofuran (THF), dimethoxyethane and 1,4-dioxane. Illustrative amide solvents are N,N-dimethylformamide (DMF) and N,N-dimethylacetamide (DMAC). Illustrative halogenated hydrocarbon solvents are chloroform, methylene chloride and 1,2-dichloroethane (EDC). In addition, water, acetonitrile, acetic acid esters, acetone and the like can also be mentioned. These solvents may be used either singly or in combination. Among these solvents, preferred are alcoholic solvents such as methanol, ethanol, propanol and isopropanol (IPA); aromatic hydrocarbon solvents such as toluene and xylene; and mixed solvents of these solvents and water.

As a hydrogen source, ammonium formate can also be used instead of hydrogen gas. The amount of ammonium formate may be in a range of from 1 to 15 molar times, preferably from 2 to 5 molar times or so relative to the molar number of the compound (IV).

The reaction temperature may differ depending upon the base and solvent to be used, but may range from −78° C. to the boiling temperature of the solvent, preferably from room temperature to 80° C. The reaction time may be in a range of from 1 to 24 hours, preferably in a range of from 2 to 16 hours.

Step (e)

The step (e) is a step in which the compound (VII) is obtained by reacting the compound (V) with the methylenemalonate compound of the formula (VI).

Usable examples of the methylenemalonate compound (VI) can include diethyl ethoxymethylenemalonate and dimethyl methoxymethylenemalonate.

This reaction can be practiced, for example, by using the methylenemalonate compound(VI) preferably in an equimolar or greater amount relative to the compound (V) and then either heating them at 100 to 180° C. or so under stirring in a solventless manner or heating them under reflux in an appropriate solvent.

No particular limitation is imposed on the solvent upon conducting the above reaction, insofar as it is inert to the reaction. Illustrative of the solvent are hydrocarbons such as benzene, toluene, xylene, n-hexane, cyclohexane and n-pentane; lower alcoholic solvents such as methanol, ethanol, propanols and butanols; ethers such as diethyl ether, tetrahydrofuran, dioxane and 1,2-dimethoxyethane; amides such as N,N-dimethylformamide, N,N-dimethylacetamide and N-methyl-2-pyrrolidone; and aprotonic polar solvents such as dimethyl sulfoxide and sulfolane. When a solvent is used, the reaction can be practiced at a temperature not higher than the boiling point of the solvent.

Step (f)

The step (f) is a step in which the compound (VIII) is obtained by reacting a sulfonyl compound with the compound (VII).

Usable examples of the sulfonyl compound can include p-toluenesulfonyl chloride, methanesulfonyl chloride and chloromethanesulfonyl chloride.

The reaction may preferably be conducted in the presence of a base. Illustrative of the base are tertiary amines such as triethylamine, tributylamine and N,N-diisopropylethylamine; dialkylanilines such as N,N-dimethylaniline and N,N-diethylaniline; heterocyclic amines such as pyridine, N,N-dimethylaminopyridine and N-methylmorpholine; and 1,8-diazobicyclo[5,4,0]undecene.

When a solvent is used, an aprotonic solvent is desired. Illustrative of the aprotonic solvent are ethers such as diethyl ether, tetrahydrofuran, dioxane and 1,2-dimethoxyethane; amides such as N,N-dimethylformamide, N,N-dimethylacetamide and N-methyl-2pyrrolidone; and chlorinated hydrocarbons such as dichloromethane, chloroform and 1,2-dichloroethane. The reaction temperature may preferably 0 to 100° C. or so.

Step (g)

The step (g) is a step in which the compound (IX) is obtained by subjecting the compound (VIII) to a ring-closing reaction under basic conditions.

A base usable in the ring-closing reaction can be either an inorganic base or an organic base. Examples of the inorganic base can include metal hydroxides such as lithium hydroxide, sodium hydroxide and potassium hydroxide; metal carbonates such as lithium carbonate, sodium carbonate and potassium carbonate; and metal hydrogencarbonates such as sodium hydrogencarbonate and potassium hydrogencarbonate. Examples of the organic base, on the other hand, can include tertiary alkylamines such as triethylamine, tributylamine and N,N-diisopropylethylamine; dialkylanilines such as N,N-dimethylaniline and N,N-diethylaniline; heterocyclic amines such as pyridine, N,N-dimethylaminopyridine and N-methylmorpholine; metal alkoxides such as sodium methoxide, sodium ethoxide, sodium isopropoxide and potassium tert-butoxide; and further, 1,8-diazobicyclo[5,4,0]undecene and N-benzyltrimethylammonium hydroxide.

Illustrative of a reaction solvent are lower alcohols such as methanol, ethanol, propanols and butanols; ethers such as diethyl ether, tetrahydrofuran, dioxane, 1,2-dimethoxyethane, 2-methoxyethyl ether and ethylene glycol diethyl ether; amides such as N,N-dimethylformamide, N,N-dimethylacetamide and N-methyl-2-pyrrolidone; and aprotonic polar solvents such as dimethyl sulfoxide and sulfolane.

The reaction can be practiced at a temperature in a range of from room temperature to 150° C.

It is effective for the ring-closing reaction to add, as a reaction promoter, potassium iodide, sodium iodide, a crown ether or the like in an amount of $\frac{1}{20}$ equivalent or more relative to the propoxybenzene compound.

Step (h)

The step (h) is a step in which the compound (X) is obtained by heating the compound (IX) in the presence or absence of a boron compound.

When the reaction is conducted in the absence of the boron compound, a compound of the formula (X) in which $R^6$ is a $C_1$–$C_6$ alkyl group is obtained. When the reaction is carried out in the presence of the boron compound, a compound of the formula (X) in which $R^6$ is a $BZ_2$. Specific examples of the boron compound can include boron trifluoride-tetrahydrofuran complex and boron trifluoride-diethyl ether complex.

The reaction in the absence of the boron compound may preferably be conducted by heating the compound (IX) at 100° C. to 200° C. in a solvent such as polyphosphoric acid. The reaction in the presence of the boron compound, on the other hand, may preferably be conducted in a solvent such as acetic anhydride or propionic anhydride by adding a chelating agent such as boron trifluoride-tetrahydrofuran complex and boron trifluoride-diethyl ether complex and heating the compound (IX) at 150° C. to 200° C.

Step (i)

The step (i) is a step in which the compound (XI) is obtained by reacting the compound (X) with 4-methylpiperazine. When $R^6$ in the formula (X) is a $C_1$–$C_6$ alkyl group, it is preferred to react 4-methylpiperazine after hydrolyzing the compound (X) into its corresponding carboxylic acid under basic or acidic conditions.

The reaction may preferably be conducted in the presence of a base. This base may be either an inorganic base or an organic base. Illustrative of the inorganic base are the carbonates and hydrogencarbonates of alkali metals and alkaline earth metals. Illustrative of the organic base are trialkylamines and nitrogen-containing heterocyclic compounds. Specifically, triethylamine, tributylamine, ethyldiisopropylamine, 4-methylmorpholine, dimethylamino-pyridine, 4-methylpiperazine or the like may be used in an excess amount such that it also serve as a reaction solvent. This reaction may be conducted using a solvent, for example, dimethyl sulfoxide.

Step (j)

The step (j) is a step in which the compound (XII) is obtained by hydrolyzing the compound (XI).

This hydrolyzing reaction can be conducted, for example, by heating the compound (XI) in the presence of a base in an aprotonic solvent. For example, heating in the presence of a trialkylamine in an alcoholic solvent may be mentioned as illustrative conditions. Specifically, the hydrolyzing reaction can be effected by simply heating the compound (XI) under stirring in the presence of triethylamine in ethanol.

A compound of the formula (XII) in which $X^1$ is a fluorine atom is levofloxacin.

EXAMPLES

The present invention will hereinafter be described more specifically based on Examples and Comparative Examples. It should, however, be borne in mind that the present invention is by no means limited to the Examples.

The optical purity (% ee) of each compound obtained was determined by subjecting it to HPLC or GC. The absolute configuration of each compound obtained was determined by comparing it with its corresponding sample of a known absolute configuration synthesized in a different manner.

Example 1

(R)-Ethyl 2-benzyloxypropionate

Ethyl 2-benzyloxypropionate (300 mg) was suspended in 0.1 M phosphate buffer (pH 6.5) (30 mL). "Lipase Fine Grade" (trade name, product of SEIKAGAKU CORPORATION, *Rhizopus delemer;* 6 mg) was added, followed by stirring at 30° C. for 24 hours. Ethyl acetate was added to the reaction mixture, denatured proteins were removed by filtration through celite. The mixture was adjusted to pH 7.0 with a 1 N aqueous solution of sodium hydroxide, followed by extraction. The organic layer was washed with a 5% aqueous solution of sodium hydrogencarbonate, and then dried over anhydrous sodium sulfate. The solvent was distilled off to afford the title compound as an oil (102 mg, 98.8% ee).

$^1$H-NMR (CDCl$_3$) δ: 1.30 (3H, t, J=6.8 Hz), 1.44 (3H, d, J=6.8 Hz), 4.05 (1H, q, J=6.8 Hz), 4.22 (1H, q, J=6.8 Hz), 4.23 (1H, q, J=6.8 Hz), 4.45 (1H, d, J=11.7 Hz), 4.67 (1H, d, J=11.7 Hz) 7.23–7.42 (5H, m)

Example 2

(R)-2-Benzyloxy-1-propanol

At 40° C., sodium borohydride (21.8 mg) was suspended in toluene (0.8 mL), and to the resulting solution, a solution of the (R)-ethyl 2-benzyloxypropionate (100 mg, 98.8% ee), which had been obtained in Example 1, in toluene (0.8 mL) was added. MeOH (0.15 mL) was added to the reaction mixture, followed by stirring at the same temperature for 3 hours. Water was added to the reaction mixture, and the resultant mixture was extracted with toluene. The organic layer was washed with water and a saturated aqueous solution of ammonium chloride, and then dried over anhydrous magnesium sulfate. After the solvent was distilled off, the residue so obtained was subjected to chromatography on a silica gel column to afford the title compound as an oil (79 mg, 99% ee).

$^1$H-NMR (CDCl$_3$) δ: 1.17 (3H, d, J=6.3 Hz), 2.20 (1H, b s), 3.43–3.72 (3H, m), 4.48 (1H, d, J=11.7 Hz), 4.64 (1H, d, J=11.7 Hz), 7.22–7.44 (5H, m)

Referential Example 1

*Microbacterium laevaniformas* (IFO 14471) was inoculated to nutrient broth (100 mL, in a Sakaguchi flask), and was cultured overnight at 30° C. under shaking. Cells were collected by centrifugation, and then lyophilized to obtain lyophilized cells of IFO 14471.

Example 3

(R)-Ethyl 2-benzyloxypropionate

Ethyl 2-benzyloxypropionate (2.0 g, 9.6 mmol) was suspended in 0.1 M phosphate buffer (pH 7.0)(100 mL). Lyophilized cells (100 mg) of IFO 14471 prepared as described in Referential Example 1 were added, followed by stirring at 30° C. Because the pH progressively dropped (as a result of formation of the carboxylic acid) as the reaction proceeded, 1 N sodium hydroxide was added to maintain the pH in the system between 6.8 an 7.2. After reacted for 14 hours, ethyl acetate (100 mL) was added. Subsequent to stirring for a while, the cells were removed by filtration through celite. After allowed to separate into layers, further extraction was conducted with ethyl acetate (100 mL). The ethyl acetate layer was collected, and then washed twice with a 5% aqueous solution of sodium hydrogencarbonate to completely remove the carboxylic acid. The organic layer was dried, and the solvent was distilled off to afford the title compound [0.93 g (46.5%), 99.9% ee]. $^1$H-NMR spectrum data of the compound were in conformity with those of the compound in Example 1.

Example 4

(R)-Ethyl 2-benzyloxypropionate

Ethyl 2-benzyloxypropionate (2.0 g, 9.6 mmol) was suspended in 0.1 M phosphate buffer (pH 7.0)(100 mL). Lyophilized cells (100 mg) of ATCC 14579 prepared in a similar manner as in Referential Example 1 were added, followed by stirring at 30° C. Because the pH progressively dropped (as a result of formation of the carboxylic acid) as the reaction proceeded, 1 N sodium hydroxide was added to maintain the pH in the system between 6.8 an 7.2. After reacted for 16 hours, ethyl acetate (100 mL) was added. Subsequent to stirring for a while, the cells were removed by filtration through celite. After allowed to separate into layers, further extraction was conducted with ethyl acetate (100 mL). The ethyl acetate layer was collected, and then washed twice with a 5% aqueous solution of sodium hydrogencarbonate to completely remove the carboxylic acid. The organic layer was dried, and the solvent was distilled off to afford the title compound [0.88 g (44.0%), 99.9% ee]. $^1$H-NMR spectrum data of the compound were in conformity with those of the compound in Example 1.

Example 5

Ethyl 2-benzyloxypropionate (racemization step)

The water layer at the time of the extraction with ethyl acetate in Example 3 was collected in its entirety, and was then adjusted to pH 2 with 10% hydrochloric acid. The water layer was then extracted twice with ethyl acetate (100 mL). After the organic layers were combined and dried, the solvent was distilled off to obtain (S)-benzyloxypropionic acid [0.83 g (48.0%), 96% ee]. An aliquot (0.8 g, 4.4 mmol) of the (S)-benzyloxypropionic acid was dissolved in ethanol (10 mL), followed by the addition of concentrated sulfuric acid (0.01 mL). The thus-prepared mixture was then heated under reflux. Eight hours later, the solvent was distilled off, and the residue was extracted with ethyl acetate (20 mL). The extract was washed with a 5% aqueous solution of sodium hydrogencarbonate (10 mL) and water (10 mL), the organic layer was dried, and the solvent was distilled off to obtain (S)-ethyl benzyloxypropionate. It was dissolved in toluene (10 mL), and under ice-cooled stirring, sodium ethoxide (0.33 g, 1.1 eq) was added, followed by stirring at room temperature for 14 hours. By gas chromatography making use of an optically active column, completion of the racemization was confirmed. Thereafter, the reaction mixture was added dropwise into a 10% aqueous solution of citric acid (10 mL). After the organic layer was washed with water (10 mL) and then dried, the solvent was distilled off to afford the title compound (0.74 g). $^1$H-NMR spectrum data of the compound were in conformity with those of the compound in Example 1. This racemate can be used as a feed for such asymmetric ester hydrolysis as in Examples 1 to 4.

Comparative Example 1

(R)-Methyl 2-benzyloxypropionate

At −30° C., benzyl bromide (9.86 g) and 60% sodium hydride (2.11 g) were dissolved in a mixed solution of dimethyl formamide (DMF) and tetrahydrofuran (THF) (50 mL, 3:2 volume ratio). (R)-Methyl lactate (5.0 g, 99% ee) was added to the solution. At the same temperature, the resultant mixture was stirred for 30 minutes. Thereafter, the mixture was stirred at room temperature for 30 minutes and further at 50° C. for 30 minutes. Water and diisopropyl ether were added to the reaction mixture, and the organic layer was washed with water and then dried over anhydrous magnesium sulfate. After the solvent was distilled off, the resultant residue was subjected to chromatography on a silica gel column to afford the title compound as a yellow oil (8.87 g, 92.1% ee).

1H-NMR (CDCl$_3$) δ: 1.44 (3H, d, J=6.8 Hz), 3.75 (3H, s), 4.07 (1H, q, J=6.9 Hz), 4.45 (1H, d, J=11.7 Hz), 4.69 (1H, d, J=11.7 Hz), 7.22–7.37 (5H, m)

Example 6

(R)-3,4-Difluoro-2-(2-benzyloxypropoxy)nitrobenzene

Under ice cooling, potassium hydroxide (5.40 g) and potassium carbonate (3.33 g) were suspended in toluene (180 mL). To the resulting suspension, a solution of (R)-2-benzyloxy-1-propanol (4.0 g), which had been obtained as in Example 2, and 2,3,4-trifluoronitrobenzene (4.13 g) in toluene (40 mL) was added, followed by stirring at the same temperature for 1 hour. Water was added to the reaction mixture, followed by extraction with toluene. The organic layer was washed with water and then dried over anhydrous magnesium sulfate. After the solvent was distilled off, the resulting residue was subjected to chromatography on a silica gel column to afford the title compound as a yellow oil (7.55 g).

1H-NMR (CDCl$_3$) δ: 1.29 (3H, d, J=6.4 Hz), 3.93–4.03 (2H, m), 4.53–4.65 (2H, m), 6.90–6.99 (1H, m), 7.23–7.35 (5H, m), 7.60–7.66 (1H, m)

Example 7

(R)-3,4-Difluoro-2-(2-benzyloxypropoxy)nitrobenzene

Under ice cooling, sodium tert-butoxide (63.6 mg) was suspended in toluene (0.5 mL). To the resulting suspension, (R)-2-benzyloxy-1-propanol (100 mg) which had been obtained as in Example 2 was added. The thus-obtained suspension was then added under ice cooling to a solution of 2,3,4-trifluoronitrobenzene (103.5 mg) in toluene (0.5 mL), followed by stirring for 1 hour. Water was added to the reaction mixture, followed by extraction with toluene. The organic layer was washed with water and then dried over anhydrous magnesium sulfate. After the solvent was distilled off, the resulting residue was subjected to chromatography on a silica gel column to afford the title compound as a yellow oil (161.2 mg). $^1$H-NMR spectrum data of the compound were in conformity with those of the compound in Example 6.

Example 8

(R)-3,4-Difluoro-2-(2-hydroxypropoxy)aniline

At room temperature, (R)-3,4-difluoro-2-(2-benzyloxypropoxy)nitrobenzene (1.0 g) which had been obtained as in Example 6 was dissolved in ethanol (10 mL). 7.5% Pd—C (1.0 g) was added, followed by stirring for 6 hours under a hydrogen atmosphere. After the Pd—C was filtered off, the filtrate so obtained was concentrated under reduced pressure, and the resulting residue was subjected to chromatography on a silica gel column to afford the title compound as an oil (600 mg, 99.0% ee).

$^1$H-NMR (CDCl$_3$) δ: 1.23 (3H, d, J=6.3 Hz), 3.81–4.89 (1H, m), 4.06–4.17 (2H, m), 6.37–6.44 (1H, m), 6.77–6.87 (1H, m)

Example 9

(R)-3,4-Difluoro-2-(2-hydroxypropoxy)aniline

At room temperature, (R)-3,4-difluoro-2-(2-benzyloxypropoxy)nitrobenzene (0.3 g) which had been obtained as in Example 6 was dissolved in toluene (3 mL). 10% Pd—C (90 mg) was added, followed by stirring at 80° C. for 4 hours under a hydrogen atmosphere. After the Pd—C was filtered off, the filtrate so obtained was concentrated under reduced pressure, and the resulting residue was subjected to chromatography on a silica gel column to afford the title compound as an oil (181.0 mg, 99.0% ee). $^1$H-NMR spectrum data of the compound were in conformity with those of the compound in Example 8.

Example 10

2,3-Difluoro-6-(2,2-diethoxycarbonylethenyl)-amino-[(R)-2-hydroxypropoxy]benzene At 100° C., (R)-3,4-difluoro-2-(2-hydroxypropoxy)-aniline (1.02 g), which had been obtained as in Example 8, and diethyl ethoxymethylenemalonate (1.14 g) were stirred for 1 hour without solvent. While removing occurring ethanol under slightly reduced pressure, the mixture was stirred for further 30 minutes. The reaction mixture was allowed to cool, and was then concentrated under reduced pressure. The resulting residue was subjected to chromatography on a silica gel column to afford the title compound as white crystals (1.83 g, 99.0% ee).

Melting point: 52–55° C. $^1$H-NMR (270 MHz, CDCl$_3$) δ: 1.22–1.46 (m, 9H), 3.55 (d, 1H, J=4.5 Hz), 3.88–4.43 (m, 7H), 6.75–7.08 (m, 2H), 8.48 (d, 1H, J=14.5 Hz)

Example 11

2,3-Difluoro-6-(2,2-diethoxycarbonylethenyl)-amino-[(R)-2-methanesulfonyloxpropoxy]-benzene 2,3-Difluoro-6-(2,2-diethoxycarbonylethenyl)amino-[(R)-2-hydroxypropoxy]benzene (3.00 g), which had been obtained as in Example 10, was dissolved in 1,2-dichloroethane (30 mL). Triethylamine (0.98 g) was added under ice-cooled stirring, and at the same temperature, methanesulfonyl chloride (1.01 g) was added further under stirring. The thus-obtained mixture was stirred at room temperature for 2 hours, and insoluble material was filtered off. The filtrate was diluted with 1,2-dichloroethane. The resultant solution was washed with water and then dried over anhydrous magnesium sulfate. Silica gel (1.5 g) was added to the dried organic layer, and subsequent to stirring for 30 minutes, insoluble material was filtered off. The solvent was distilled off under reduced pressure, and the residue was crystallized from diisopropyl ether. Crystals were then collected by filtration to afford the title compound (3.27 g).

$^1$H-NMR (CDCl$_3$) δ: 1.22–1.47 (6H, m), 1.58 (3H, d, J=7 Hz), 1.50 (3H, d, J=7 Hz), 3.13 (3H, s), 3.98–4.60 (6H, m), 4.95–5.35 (1H, m), 6.79–7.14 (2H, m), 8.41 (1H, d, J=13.5 Hz)

Example 12

(S)-Diethyl(7,8-difluoro-3-methyl-3,4-dihydro-2H-[1,4]benzoxazin-4-yl)methylene-malonate The 2,3-difluoro-6-(2,2-diethoxycarbonylethenyl)amino-[(R)-2-methanesulfonyloxypropoxy]benzene (3.00 g), which had been obtained in Example 11, was dissolved in anhydrous DMF (15 mL), followed by the addition of potassium carbonate (0.92 g). The resultant mixture was stirred at 80° C. for 2 hours. The solvent was distilled off, the residue was extracted with ethyl acetate, and the extract was washed with water and then dried over anhydrous magnesium sulfate. The solvent was distilled off under reduced pressure, and the resulting residue was subjected to chromatography on a silica gel column to afford the title compound (2.14 g).

$^1$H-NMR (CDCl$_3$) δ: 1.22–1.42 (9H, m), 3.90–4.44 (7H, m), 6.74–6.88 (2H, m) 7.78 (1H, s)

Example 13

(3S)-9,10-Difluoro-3-methyl-7-oxo-2,3-dihydro-7H-pyrido[1,2,3-de][1,4]benzoxazine-6-carboxylicacid-boron difluoride chelate complex The (S)-diethyl(7,8-difluoro-3-methyl-3,4-dihydro-2H-[1,4]benzoxazin-4-yl)methylenemalonate (2 g), which had been obtained in Example 12, and acetic anhydride (2 mL) were mixed, and at 140° C., 47% boron trifluoride-tetrahydrofuran. complex (0.8 mL) was added. At the same temperature, the resultant mixture was heated under stirring for 1 hour. After occurring low-boiling products were distilled off, the reaction mixture was allowed to cool to room temperature. Acetone (10 mL) was added to the reaction mixture, followed by stirring for 30 minutes at the same temperature. Precipitated crystals were collected and washed with acetone to afford the title compound (1.55 g).

Example 14

(3S)-(−)-9-Fluoro-3-methyl-10-(4-methyl-1-piperazinyl)-7-oxo-2,3-dihydro-7H-pyrido[1,2,3-de][1,4]benzoxazine-6-carboxylic acid (Levofloxacin)

The (3S)-9,10-difluoro-3-methyl-7-oxo-2,3-dihydro-7H-pyrido[1,2,3-de][1,4]benzoxazine-6-carboxylic acid-boron difluoride chelate complex (310 mg), which had been obtained in Example 13, was dissolved in dimethyl sulfoxide (6 mL), followed by the addition of triethylamine (0.32 mL) and N-methylpiperazine (0.13 mL). The thus-obtained mixture was stirred at room temperature for 17 hours, and was then evaporated to dryness under reduced pressure. After the residue was washed with diethyl ether, the residue was dissolved in 95% ethanol (20 mL) which contained triethylamine (0.5 mL). The solution so obtained was heated under reflux for 8 hours. The reaction mixture was allowed to cool, and was then evaporated to dryness under reduced pressure. The residue was dissolved in dilute hydrochloric acid (5%). Subsequent to addition of chloroform, the resultant mixture was allowed to separate into layers. The water layer was adjusted to pH 11 with sodium hydroxide (1 mol/L), and then to pH 7.4 with hydrochloric acid (1 mol/L). The thus-prepared mixture was extracted with chloroform (50 mL×3). The extracts were combined and dried over sodium sulfate, and the chloroform was distilled off. Resulting powder was recrystallized from ethanol-diethyl ether to afford the title compound as transparent fine needles (120 mg).

Melting point: 225–227° C. Elemental analysis for $C_{18}H_{20}FN_3O_4 \cdot \frac{1}{2}H_2O$: Calculated: C, 58.37; H, 5.72; N, 11.35. Found: C, 58.17; H, 5.58; N, 11.27.

Example 15

(1) Disruption of Cells (French Press)

ATCC 14579 cells, which had been obtained by conducting shaking culture in a Sakaguchi flask (amount of culture medium: 1,200 mL), were suspended in 20 mM phosphate buffer (80 mL)(pH 7.0; with 1 mM EDTA and DTT contained), and by a French press, a pressure of 15,000 psi was applied to disrupt the cells.

The disrupted cells were centrifuged by a centrifugal separator (10,000 G, 30 min) to obtain a cell extract (85.0 mL) (total activity: 123 unit, specific activity: 0.032 unit/mg).

(2) Anion Exchange Chromatography

The cell extract was fractionated under the below-described anion exchange chromatographic purification conditions. Individual fractions were measured for hydrolytic activity against ethyl 2-benzyloxypropionate to obtain active fractions (206 mL)(total activity: 88 unit, specific activity: 0.058 unit/mg, activity yield: 72%).

Anion exchange chromatographic purification conditions
  Carrier: "Source Q" (trade name, product of Pharmacia Biotech, Inc.) 400 mL
  Column: 50 mm diameter by 200 mm height
  Mobile phase:
    Solution A: 20 mM phosphate buffer (pH 7.0, with 1 mM EDTA and DTT contained) 900 mL
    Solution B: Solution A+1.0 M NaCl, 900 mL
  A→B linear gradient elution
    Detection: 280 nm; temperature: 4° C. 15 min. fractions were collected, each followed by hydrolysis against ethyl 2-benzyloxypropionate.

(3) Hydrophobic Chromatography

To the active fractions (206 mL) collected by the anion exchange chromatography, ammonium sulfate (54.4 g, equivalent to 2.0 M) was added in small portions. After stirred for 30 minutes, the resulting precipitate was removed by centrifugation (10,000 G, 30 min). The thus-obtained supernatant was fractionated under the below-described hydrophobic chromatographic purification conditions. Individual fractions were measured for hydrolytic activity against ethyl 2-benzyloxypropionate, and active fractions (251–308 min) were ascertained. Those fractionated active fractions were desalted and concentrated by ultrafiltration to obtain an active center fraction (1.0 mL) (total activity: 16.8 unit, specific activity: 3.23 unit/mg, activity yield: 19%).

Hydrophobic chromatographic purification conditions
Carrier: "Resource ETH" (trade name, product of Pharmacia Biotech, Inc.) 100 mL
Column: 45 mm diameter by 60 mm height
Mobile phase:
Solution A: 20 mM phosphate buffer (pH 7.0, with 1 mM EDTA and DTT contained) 600 mL
Solution B: Solution A+2.0 M Ammonium sulfate, 600 mL
B→A linear gradient elution
Detection: 280 nm; temperature: 4° C. 7 min. fractions were collected, each followed by hydrolysis against ethyl 2-benzyloxypropionate.

(4) Anion Exchange Chromatography ("Mono Q", trade name, product of Pharmacia Biotech, Inc.)

The active fraction (1.0 mL), which had been collected by the hydrophobic chromatography, was fractionated by anion exchange chromatography on "Mono Q". Individual fractions were measured for hydrolytic activity against ethyl 2-benzyloxypropionate, and active fractions (23–25 min) were ascertained. Those fractionated active fractions were desalted and concentrated by ultrafiltration to obtain an active center fraction (1.0 mL) (total activity: 5.9 unit, specific activity: 4.54 unit/mg, activity yield: 35%). That active protein was found to have a molecular weight of about 38,000 (SDS PAGE) or about 40,000 (gel filtration).

Anion exchange chromatographic purification conditions ("Mono Q")
Column: Anion exchange column ("Mono Q") 1 mL
Mobile phase:
Solution A: 20 mM phosphate buffer (pH 7.0)
Solution B: Solution A+1.0 M NaCl
A→B linear gradient elution
Flow rate: 1.0 mL/min.
Detection: 280 nm
Temperature: room temperature 1 min. fractions were collected, each followed by hydrolysis against ethyl 2-benzyloxypropionate.

Isolation and Purification Results of ATCC 14579

|  | Amount of proteins (mg) | Total activity (unit) | Specific activity (unit/mg) | Activity yield (%) |
|---|---|---|---|---|
| Extract | 3893 | 123 | 0.032 | 100 |
| Anion exchange chromatography | 1508 | 88 | 0.058 | 72 |
| Hydrophobic chromatography | 5.2 | 16.8 | 3.23 | 14 |
| "Mono Q" | 1.3 | 5.9 | 4.54 | 4.8 |

Using the microorganism-derived, purified enzyme obtained as described above, an asymmetric ester-hydrolyzing reaction was conducted as in Examples 1, 2, 3 and 4. Ethyl (R)-2-benzyloxypropionate of 99% ee or higher in optical purity was efficiently obtained.

INDUSTRIAL APPLICABILITY

According to the process of the present invention, an optically active propoxyaniline derivative (V) having high optical purity can be obtained through fewer steps, at a lower cost. Thus, this invention provides an industrially advantageous method for producing a levofloxacin compound, which has a high quality of optical purity and is thus useful as an antimicrobial agent.

What is claimed is:

1. A process for producing an optically active compound represented by the following formula (I-a):

(I-a)

wherein $R^1$ represents an alkyl group having 1 to 6 carbon atoms and $R^2$ represents a hydroxyl-protecting group, said hydroxyl-protecting group is selected from the group consisting of a substituted or unsubstituted alkoxycarbonyl group, a substituted or unsubstituted aralkyloxycarbonyl group, a substituted or unsubstituted acyl group, a substituted or unsubstituted alkyl group, a substituted or unsubstituted alkenyl group, a substituted or unsubstituted aralkyl groups, and a silyl group substituted by one or more alkyl group and/or aralkyl group;

which comprises:

treating a compound, which is represented by the following formula (I):

(I)

wherein $R^1$ and $R^2$ have the same meanings as defined above, with an enzyme having asymmetric ester-hydrolyzing ability obtained from a microorganism, a cultured medium of said microorganism having asymmetric ester-hydrolyzing ability, cells of said microorganism or a processed product of cells of said microorganism to obtain a mixture; and isolating and collecting said optically active compound (I-a) from said mixture;

wherein said microorganism is selected from the group consisting of Bacillus bacteria, Microbacterium laevaniformas IFO 14471, Micrococcus bacteria, Pseudomonas bacteria, and Streptomyces bacteria.

2. The process according to claim 1, wherein $R^2$ is a substituted or unsubstituted aralkyl group.

3. The process according to claim 1 or 2, wherein $R^2$ is a benzyl group.

4. The process according to claim 1, wherein $R^2$ is an ethyl group.

5. The process according to claim 1 or 2, wherein said enzyme is lipase.

6. The process according to claim 1, wherein said bacterium is a *Micrococcus* bacteria.

7. The process according to claim 1, wherein said bacterium is a *Bacillus* bacterium.

8. The process according to claim 1, wherein said bacterium is *Bacillus cereus*.

9. The process according to claim 8, wherein said bacterium is *Bacillus cereus* DSC 0007, *Bacillus cereus* ATCC 14579, or *Microbacterium laevaniformas* (IFO 14471).

10. The process according to claim 1, wherein said enzyme has asymmetric ester-hydrolyzing ability and is obtained by disrupting cells of a microorganism, which has asymmetric ester-hydrolyzing ability, under high pressure and then purifying the thus-disrupted cells successively by strong anion chromatography, hydrophobic chromatography and strong anion chromatography.

11. The process according to claim 1, wherein said bacterium is a *Pseudomonas* bacteria.

12. The process according to claim 1, wherein said bacterium is a *Streptomyces* bacteria.

* * * * *

UNITED STATES PATENT AND TRADEMARK OFFICE
CERTIFICATE OF CORRECTION

PATENT NO. : 7,217,560 B2 Page 1 of 1
APPLICATION NO. : 10/469827
DATED : May 15, 2007
INVENTOR(S) : Kouji Sato et al.

It is certified that error appears in the above-identified patent and that said Letters Patent is hereby corrected as shown below:

Col. 24, lines 45-48 ;

In claim 1, formula (I) :

" 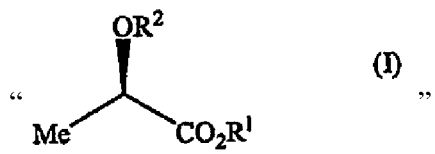 (I) "

should read

-- 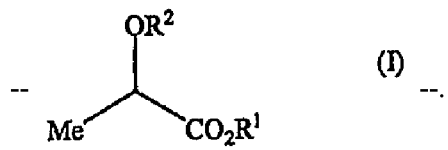 (I) --.

Signed and Sealed this

Twenty-eighth Day of August, 2007

JON W. DUDAS
*Director of the United States Patent and Trademark Office*